United States Patent [19]
Bolta et al.

[11] Patent Number: 6,139,164
[45] Date of Patent: Oct. 31, 2000

[54] ADJUSTABLE MOBILE LIGHT PANEL STAND

[75] Inventors: Charles J. Bolta, 625 Mathews St., Fort Collins, Colo. 80524; Francis M. Wile, Belview, Colo.

[73] Assignee: Charles J. Bolta, Fort Collins, Colo.

[21] Appl. No.: 09/283,341

[22] Filed: Mar. 31, 1999

[51] Int. Cl.$^7$ ............................................. G09F 13/04
[52] U.S. Cl. ............................ 362/97; 362/418; 248/454
[58] Field of Search ............................ 362/417, 418, 362/419, 426, 427, 430, 449, 804, 269, 270, 275, 285, 287, 97; 248/454, 122.1, 124.1; 607/88, 89, 90, 91, 92, 93, 94, 95

[56] References Cited

U.S. PATENT DOCUMENTS

| | | | |
|---|---|---|---|
| 4,631,643 | 12/1986 | Koster | 362/97 |
| 4,803,606 | 2/1989 | Rotter | 362/250 |
| 5,060,118 | 10/1991 | Penrod | 362/1 |
| 5,308,035 | 5/1994 | Ross | 248/454 |
| 5,725,192 | 3/1998 | Cloninger | 248/458 |

*Primary Examiner*—Sandra O'Shea
*Assistant Examiner*—Hargobind S. Sawhney
*Attorney, Agent, or Firm*—Rick Maritn; Patent Law Offices of Rick Martin, P.C.

[57] ABSTRACT

A mobile light panel stand supports a light panel suited to treat humans who are in need of exposure to light in a manner known as light therapy. The stand has two pair of hinged legs. Each pair of legs has a brace member to provide a solid two-legged assembly. The two two-legged assemblies are connected by collapsible braces which allow the device to fold into a narrow posture for passage through doorways. The base of the opened assembly has an anti-tipping wide stance for use by hospitals where patients may lean on the device for support. One set of legs has an upper extension which supports the light panel between the two two-legged assemblies via adjustable nuts and bolts. The light panel can be tilted by adjusting the adjustable nuts. In the preferred embodiment the angle between the front and rear H shaped support legs is adjustable between zero and 180 degrees. This feature coupled with a smaller width light panel and H frame stance and wheel braces makes the device suitable for mechanics' work areas where a low stance of the light panel can light a brake repair job. The light stand itself can be adjusted up and down along its support legs.

20 Claims, 4 Drawing Sheets

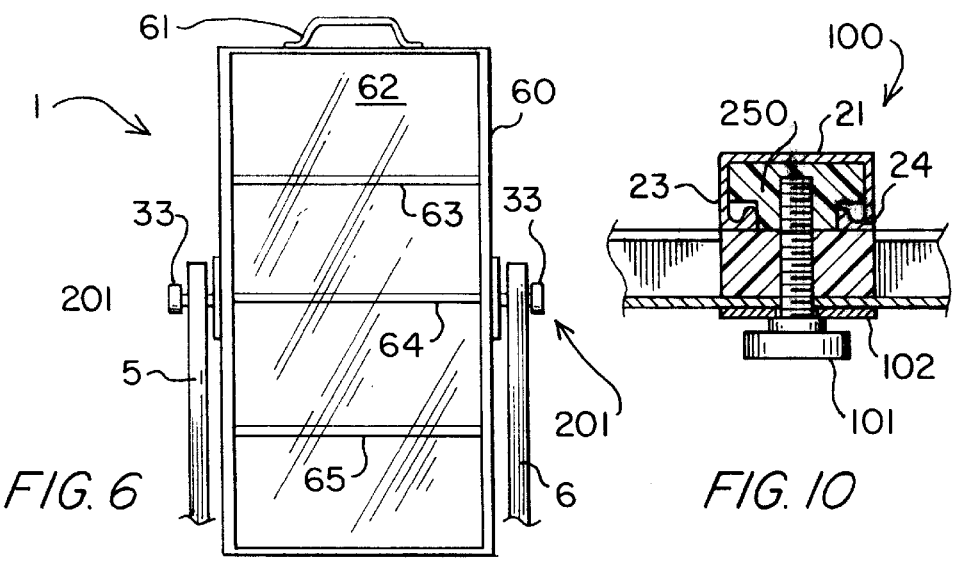
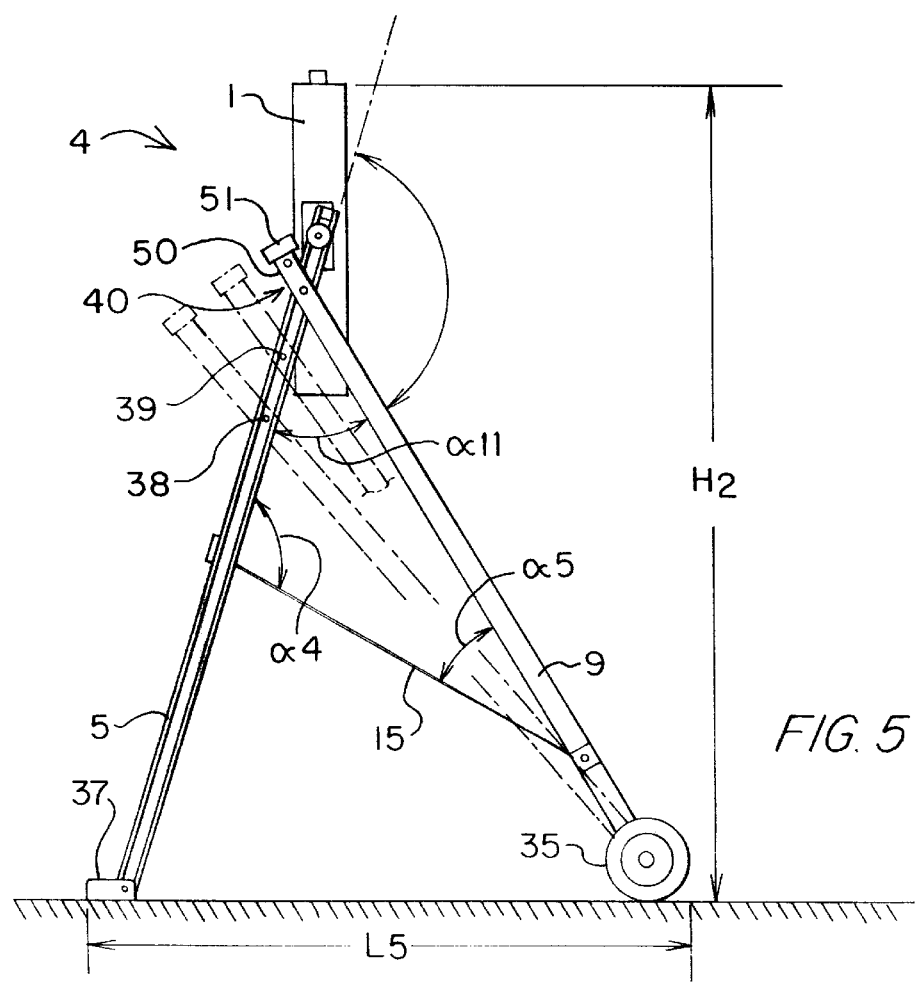

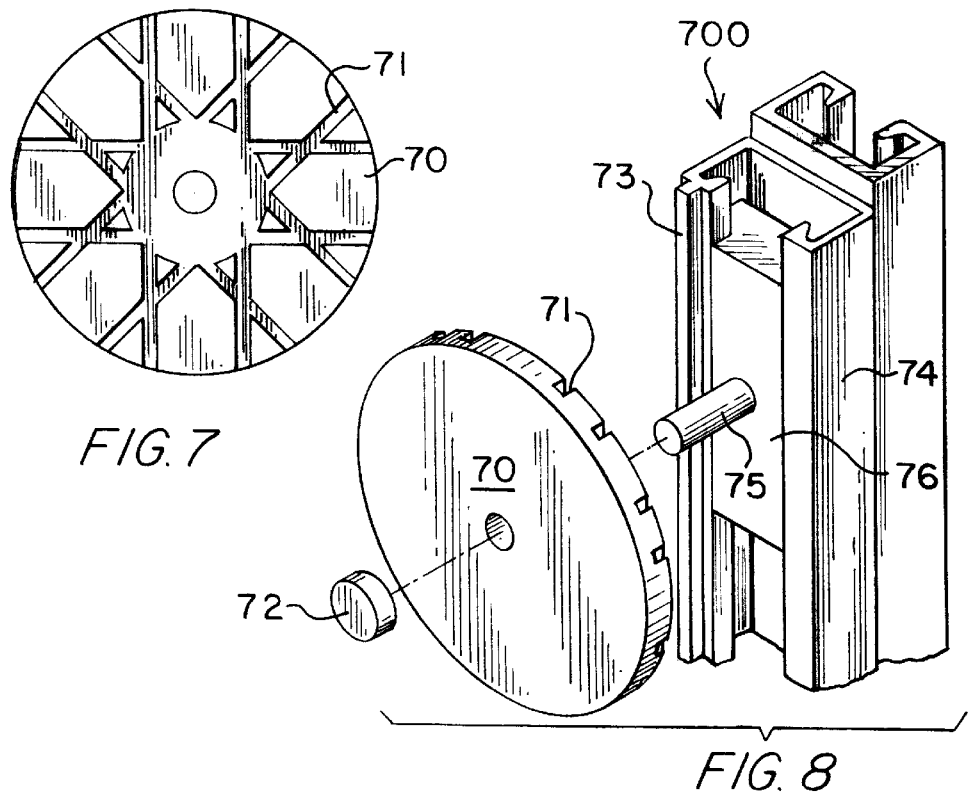
FIG. 7
FIG. 8
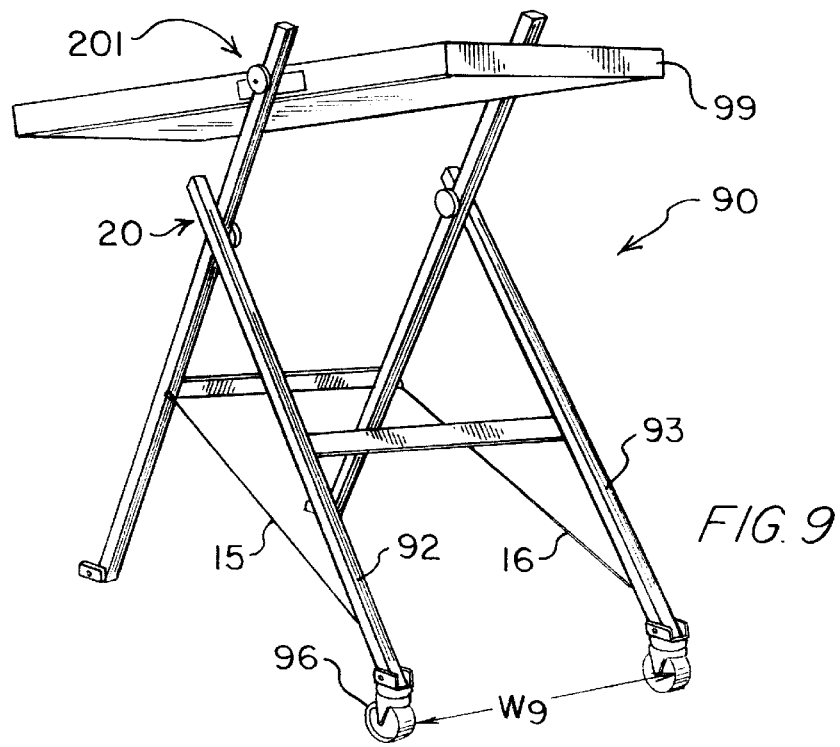
FIG. 9

ADJUSTABLE MOBILE LIGHT PANEL STAND

FIELD OF INVENTION

This invention generally relates to the field of industrial lighting and treatment for a light deficiency medical disorder. Specifically, the system relates to the efficient placement and effective utilization of industrial grade light panels. Through the invention Seasonal Pattern or Seasonal Affect Disorder may be treated efficiently and effectively by subjecting the patient to an electroluminescent lighting source. This source may be a full-spectrum and/or high-lumen output light positioned within an institutional frame. The system also can act to simultaneously shield the patient from certain undesirable electromagnetic fields (EMFs). The invention also has been found to benefit shop workers where light is lacking ranging from under a vehicle on a rack or lighting inside engine compartment or brake work. The range of adjustable heights and forward stance makes shop work faster, less stressful and safer.

BACKGROUND OF THE INVENTION

Little information appears presently available with respect to treating Seasonal Pattern or Seasonal Affect Disorder. Basically, the disorder appears treatable to some extent by subjecting the patient to a full-spectrum light; that is a light which emits throughout the visible spectrum at wavelengths approaching the spectrum at which the sun's light reaches the surface of the earth; that is the wavelengths to which man has been subjected throughout evolution. While this appears simple enough, in actual practice, problems of both a mechanical and electromagnetic nature have not as yet been appropriately addressed.

Problems of a mechanical nature encountered in providing such a system included the type of frame and support structure needed to withstand institutional (i.e., hospitals, nursing homes, shops, etc.) use. It was determined that: a) the frame needed to be foldable for storage; b) the light box removable; c) the entire unit be easily moved from room to room; d) there be no sharp edges, and counter-sunk bolts be used for safety; e) it not be able to be pulled or tipped over; f) the unit be able to be assembled and moved by one person; g) and the unit be strong enough that it would not collapse while in use.

In further considering the nature and effectiveness of the treatment, the question arose as to how to properly shield the EMFs emanating from the lights. It was determined that as there is potentially compelling scientific evidence that suggests that exposure to EMFs may not only generally cause physical and emotional disorders in human beings, but that these impacts might negatively impact the specific treatment being implemented in this case. Thus, it is preferred that the system act to reduce these fields as much as possible.

As to the framing and support elements, other frames were reviewed yet found unusable due to their large size and weight. They were unsuitable for use in many institutional settings i.e., hospitals or other kinds of treatment clinics and shops where space is at a premium. Generally, the requirements for institutional settings are such that any device must be sturdy, strong, movable, and foldable. There is, therefore, a need for a structure that is easily cleansed, requires low maintenance, and is able to hold a large light box specifically designed for institutional use.

Other factors taken into consideration in designing this apparatus were that it would be preferable for it to be easily repaired and cleaned. Also, it should not fall over when in use.

To solve the mechanical problems at hand, it was determined that a light was needed which could be quickly and efficiently positioned, allow simple operation, and abundantly illuminate the area where such persons as are using it are seated or working.

One aspect of the invention is that it can, to some degree, be characterized as presenting techniques and devices others might have had the opportunity to try. This may actually highlight the non-obvious nature of the invention. Although the implementing arts and elements had long been available, those involved in this field simply did not appreciate that the use of these elements was something they could use as effectively as shown here. This can also be surprising because there has been a long felt but unsatisfied need for the invention. Those involved in the Seasonal Pattern area have appreciated that the problem of effective treatment existed. However, the true nature of the problem was not fully seen by those skilled in the art prior to this invention. To some degree, this may have been due to the fact that those skilled in the art failed to understand the problem of properly subjecting the patient to conditions and to providing an easily usable device for treatment. The efforts undertaken may even have acted to teach away from the technical direction taken by this invention. Certainly some of the literature has even acted to not only direct persons away from the direction taken in this invention but also to even create a level of disbelief and incredulity on the part of those skilled in the art that the Patentee's approach is appropriate. In the preferred embodiment a two bulb light panel only about 15 inches wide can be supported in a forward stance a few inches off the ground and nearly as far forward as the bottom portions of the supporting front H frame legs. This allows a mechanic to light up a brake assembly right near the ground, and then adjust the H frames up high and swivel the light panel to illuminate the underside of a car that is jacked up on a lift.

SUMMARY OF THE INVENTION

The main aspect of the present invention fulfills the requirements outlined above. The system may include a foldable, lightweight, aluminum and stainless steel lighting fixture employed for use with full-spectrum lights. It may also incorporate the aspect of the lights being shielded from EMFs. The frame and support preferred is lightweight, portable, and foldable for easy use and storage. The channeled support legs are opened with a sliding block making it possible for one person to safely assemble it by sliding the light source or frame legs into different heights and/or forward stances of the lighting fixture.

This invention can also include a foldable stand mounted on wheels and wheel foot supports to allow for mobility, front and rear supports, and a light box with shielding for EMFs. The frame can be made of aluminum and stainless steel, and the unit can be designed to be cleaned with minimum effort. All the parts involved in making the unit may be special made or be obtained from existing manufacturers. The unique structure of the frame ensures that a large or small light box can be placed upon it and used.

For safety a sliding lock friction bar can be used inside an open channel support leg. The legs are designed to insure that the unit will not tip over when in use as they may provide a broad base of support for the unit as a whole. Large, perhaps even four-inch, tightening-down handles can be employed on either side of the unit so that when the light box unit is placed within the channeled legs and the end stop is in place, there is no possibility of the light box unit somehow slipping out.

In order to provide a wide base of support, front and rear horizontal supports have been developed. The sliding channel mounting system gives a solid place upon which the light box may be placed and allows for one-person assembly. The tether leg supports enable the entire invention to be folded up easily by one person. The tether also provide added support to the unit as a whole in the forward stance position. The wheels are particularly durable, and the wheel support foot gives an added safety feature to the unit. Upon consideration of all factors, it may be desirable that in order to provide the best mode of light possible, the light box may preferably contain either full-spectrum, high lumen, lux, or foot-candle bulbs. This may be preferable because the person utilizing this invention may have specific preferences as to the type of light they will receive from it. The inclusion of a parabolic lens makes it possible for the EMFs to be reduced from the front of the unit. It has been found that treatment in this way provides the best mode of alleviating the condition. The person receiving the light is not also being subjected to EMF emissions.

The light box is supported in such a way that allows the light box to be angled as needed and/or adjusted up and down in height along the H frame. This way, the person using the light has the maximum amount of light possible. The forward positioning of the light box also allows the light to be moved as close as possible to the person using it or the object being lighted. The front horizontal support bar allows the light box to swing freely and also adds substantial support strength. The design is strong. For instance, the inventors were able to stand on the support frame without any signs of collapse or damage. The front horizontal bar can be adjusted upon manufacturing to compensate for a larger or smaller light box. The front and rear horizontal support bars are placed as close as possible to the light box to give minimum width. This allows the invention to fit through doorways.

If further folding is needed for storage, one can remove the light box. The support frame can then lie flat or stand completely upright. A safety strap or bar can be used when the support frame is in an upright folded position to stop the frame from unfolding.

The pivot point has a low-friction washer between the vertical frame tubes. This allows the invention to fold easily. It can be located at different points depending upon the size of the light box being used. The handle can be tightened or loosened to hold the vertical tube supports in one of many possible positions. In this way, the invention can be moved or wheeled into tight spaces yet still be safely upright and usable. In addition, the function of wheeling the unit may be exchanged for utilizing skids when there is no need for the unit to be wheeled from place to place.

The front horizontal support bar is placed on the front legs to create an H frame. The channeled sliding block systems for both the light panel and the H frames allows maximum stance and height adjustability. The sliding block on the light box mounting system slides safely into the channeled H frame. The light box mounting plate and spindle is mounted to the light box with bolts that are flush-mounted to the plate. This allows the box to swivel frontwards and backwards 360 degrees. The nuts are placed in the light box allowing for easy assembly depending upon the size of the light box. The mounting plate can be adjusted as well, depending upon the size of the light box. There is a low-friction washer that allows the light box to be easily adjusted to varying angles by tightening or loosening the handles.

The invention can be wheeled or slid by the use of the wheel support foot. A wheel is bolted to the wheel support foot. A plate can also be bolted to the wheel support foot which would allow for a larger surface area i.e., as needed for a wood floor or rug. Low or highfriction material can be attached to the base of this plate to address the sliding of the device on various floors.

The wheel support foot attaches to the vertical support frame tube. An optional swivel type ladder foot can be used on the H frame not having the wheels. This keeps the wheels and wheel support feet parallel to the floor and engaged in a non-slip manner to the floor. The corners of the wheel support foot are rounded in the front so that there are no sharp or rough edges. The wheel support foot can also be cut back to flush-mount to the vertical support tube. The wheels can also be made to be either locking or non-locking, swivel base or stationary.

An optional parabolic lens is grounded to the metal frame of the light box with a wire. This grounding lowers the amount of measurable EMFs being emitted by the light box when turned on (as measured by the amount of 60 Hz AC voltage detectable near the surface of the lens at distances of up to one meter). This can be important because it appears that certain emissions can actually match, or at least impact, low-frequency brainwave and other biological patterns. In spite of the fact that the light can often operate at a household frequency (60 Hz), it appears that varying frequency EMFs are possible. The grounding feature on the lens structure can act as an RF filter or to otherwise serve to mitigate the effect of EMFs. It also can act to avoid allowing an impact on the patient regardless of the exact nature of the effect. The parabolic lens can also be used to maximize the amount of full-spectrum light able to come through. It has also been found that with a larger 18 cell parabolic lens in a 4'×2' fixture, the measurable EMFs are not removed to a level the inventors found satisfactory. The use of a one-inch mesh wire attached perpendicularly to the parabolic lens lowered the measurable EMFs to a satisfactory level and also allowed for a maximum amount of full-spectrum light to come through the lens. A bracket across face of a clear lens keeps tools or parts that may fall on the lens from breaking through and breaking bulbs.

An electronic ballast and radio frequency filter may be used. Further shielding may be added to reduce electromagnetic fields as much as possible. The shielding added is comprised of 0.020 nickel alloy mu metal.

Each unit comes complete with an on/off switch and a standard three-prong plug. The light box can be preassembled, or each part of the stainless steel and aluminum frame can be marked for quick assembly. Once turned on, the unit automatically produces the predetermined amount of high lumen or full-spectrum light, and the EMF emissions are reduced through proper design as discussed earlier.

In general terms, the support frame can serve as a means for the light box to be safely portable. The light box can serve as a means for performing the function of providing the closest to natural sunlight possible aiding in the treatment of Seasonal Pattern and/or providing industrial lighting.

As mentioned, the support frame can be used with many different types of light fixtures (fluorescent, halogen, incandescent, or high-intensity discharge lamp fixtures) for a variety of purposes. For the treatment of Seasonal Pattern, however, the full-spectrum light appears most effective.

The end result goals of this invention include that a person may use this invention to treat Seasonal Pattern as it provides the closest to natural sunlight possible while possibly simultaneously mitigating the potentially harmful effects of EMF emissions. Also as a shop light all these benefits accrue during daily work time. This mitigation of EMFs takes into consideration that it is believed that a person with Seasonal Pattern may already be in a deteriorated physical and/or emotional state and, therefore, more susceptible to EMFs. It is also preferred that it be able to be assembled and used by one person. Another goal is that the unit be durable enough to withstand years of institutional and commercial use.

Aluminum and stainless steel components can be used to make the unit lightweight; yet it is also possible for the framing system to be made out of other materials (including but not limited to plastic, wood, and the like). Similarly, although the description may be couched in terms of a specific kind of element (i.e., a tubular element, etc.), it should be understood to encompass all varieties of other elements as well (i.e., solid plates and other support structures). The unit is able to be washed, and all parts of the unit are able to be replaced. Being made of aluminum and stainless steel, the unit is extremely durable. The tethered leg supports provide a wide base of support for the unit, making it difficult to damage the unit by putting stress upon the framing system.

The sliding block mounting system can make it possible for one person to assemble and adjust the unit. Having the sliding block legs supports and wheels makes it functional for one person to use and move as needed. It is also uniquely suited for institutional use in that it is able to be stored with a minimum of space needed when not in use. It if is preferred that the unit take up even less space when in use and when folded up, it is possible to shorten the tether supports or even make them telescopic, thereby making the entire unit shorter when extended and when stored in its upright folded position.

In accomplishing a desired medical treatment desired, a number of steps are possible. The patient can be subjected to varying times or levels of exposure. This can be built up over the course of days or weeks or can be a limited number of gentle or intense treatments. It may be timed to coincide or be cyclincal with the patient's circadian, daily, or other biological rhythms. They may also be varied based upon meteorological conditions. The system can be implemented by analyzing the patient. This can include measuring specific characteristics of the patient. Then the treatment can include determining an appropriate treatment regimen, and then establishing the devices so as to implement that regimen. This establishment can be accomplished automatically through proper device design. This can also involve automatic or manual timing to both initiate and terminate treatment. The device may also act manually or automatically to avoid sharp changes in conditions. There can also be changes in the intensity of illumination along the surface of the light or at the patient's location if desired. Automatic positioning features can be included where it is deemed necessary either for safety or for treatment.

As mentioned, it is possible that this invention as described may be used in alternative settings i.e., as an industrial light frame for other applications, or as an artist's light. As stated in the previous paragraphs, a broad disclosure is to be understood from the foregoing discussion. Certainly, elements of the invention as described in this application may be modified or changed without changing the essential nature of the invention. The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which will be included in a full patent application.

Equivalent, broader, and more generic terms are implicit in the prior description of each element. Such terms can be substituted where desired to make explicit the implicitly broad coverage to which this invention is entitled. Further, it should be understood that a variety of changes may be made without departing from the essence of the invention. Such changes are also implicitly included in the description. They still fall within the scope of this invention. A broad disclosure encompassing both the explicit embodiments shown, the great variety of implicit alternative embodiments, and the broad methods or processes and the like are encompassed by this disclosure and may be relied upon when drafting the claims for the full patent application. It should be understood that such language changes and broad claiming will be accomplished when the Applicant later (filed by the required deadline) seeks a patent filing based on this provisional filing. The subsequently filed, full patent application will seek examination of as broad a base of claims as deemed within the Applicant's right and will be designed to yield a patent covering numerous aspects of the invention both independently and as an overall system.

In general, it is an aspect of the present invention to provide a portable, easily assembled and movable frame to hold a light box that contains full-spectrum, high lumen output bulbs, while also providing shielding from measurable electric fields.

Another aspect of the present invention is to provide full-spectrum light that provides light that is the closest to natural sunlight available. It should also provide very high lumen, lux, or foot-candle output.

Another aspect of the present invention is that the patient be shielded from the potentially harmful effects of EMF emissions. Included in the goal of shielding is reducing the measurable AC electric field through the front parabolic or other lenses, with minimal loss of light.

Another aspect of the invention is that it be large enough to hold either a light box that provides sufficient full-spectrum light or a high-intensity fixture to treat Seasonal Pattern.

Another aspect of the present invention is to provide a particularly novel sliding block system on the frame that makes it easy for one person to assemble and disassemble the lighting system.

Other aspects of this invention will appear from the following description and appended claims, reference being made to the accompanying drawings forming a part of this specification wherein like reference characters designate corresponding parts in the several views.

BRIEF DESCRIPTION OF THE DRAWINGS

FIG. 5 is a side plan view of the preferred embodiment.

FIG. 6 is a front plan view of the light panel.

FIG. 7 is a front plan view of a safety lock.

FIG. 8 is a top perspective view of the safety lock assembly.

FIG. 9 is a side perspective view of an alternate embodiment wide stand.

FIG. 10 is a sectional view of an alternate embodiment sliding lock assembly.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENT

Figure 1:
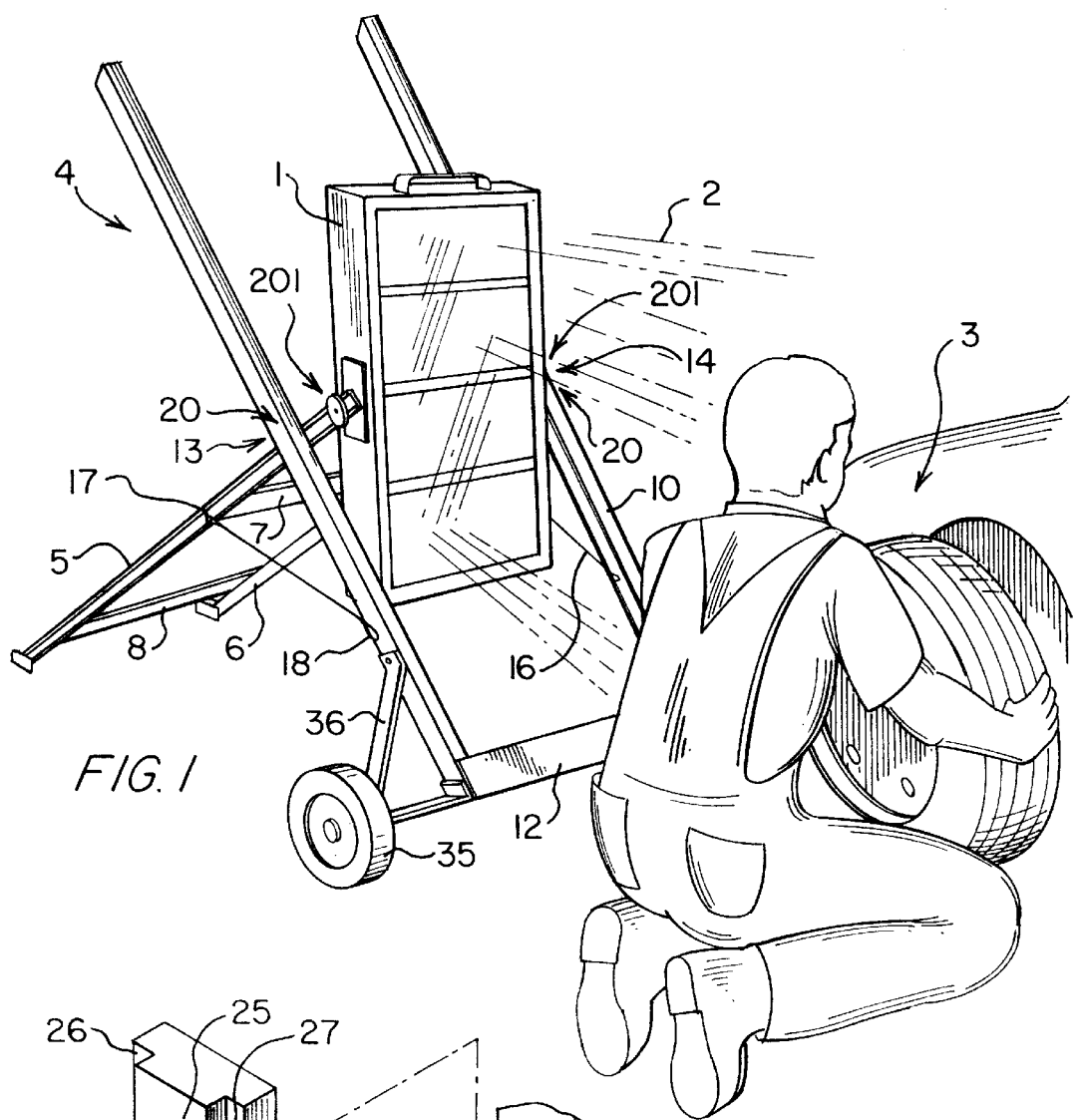
FIG. 1 is a front perspective view of the preferred embodiment on a low stance.

Referring first to FIG. 1a, a panel 1 is emitting light rays 2 to work area 3. In practice the light panel 1 could be lowered to within inches of the ground in order to provide light straight into the tire without creating any shadows in the downward direction. As shown in FIG. 3 the light panel 1 is supported forward of the stand's central plane P—P in its plane F—F. The stand 4 has a pair of parallel rear legs 5,6 which are connected by horizontal braces 7,8 which altogether form an H shaped assembly. The stand 4 also has a pair of parallel front legs 9,10 which are connected by horizontal braces 11,12 which altogether form an H shaped assembly. The two H shaped assemblies are pivotally joined at 13, 14 by a sliding lock assembly 20, equivalent to sliding block assembly 201 shown in detail in FIG. 2. Likewise the light panel 1 is supported by sliding lock assemblies 201 which are equivalent to assemblies 20, and having a brace 30. Assembly 20 has the bolt 29 affixed inside the sliding block 25 so that the light panel is tiltable in a 360 degrees rotation as well as adjustable in height along legs 5,6.

In operation the stand 4 can be folded for transport or storage with the two H assemblies essentially parallel. In use the angle between the two H assemblies is adjustable from 0 to 180 degrees with most applications using a range of 40 degrees –110 degrees.

Safety tethers 15,16 reinforce any stance which the stand 4 is locked into by locking the sliding lock assemblies 20. Preferably the safety tether 15,16 maybe of steel cable, but chains, cords, or telescoping assemblies could be used. Attachment point 17 on the rear leg 5 is higher than attachment point 18 on the front leg 9.

Figure 2:
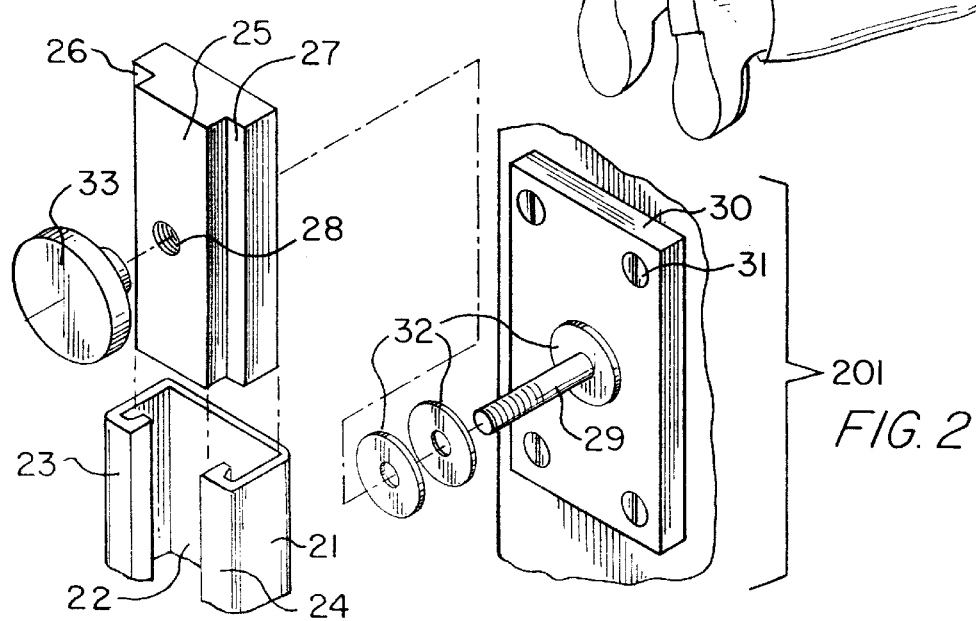
FIG. 2 is an exploded view of the sliding lock assembly.
Figure 3:
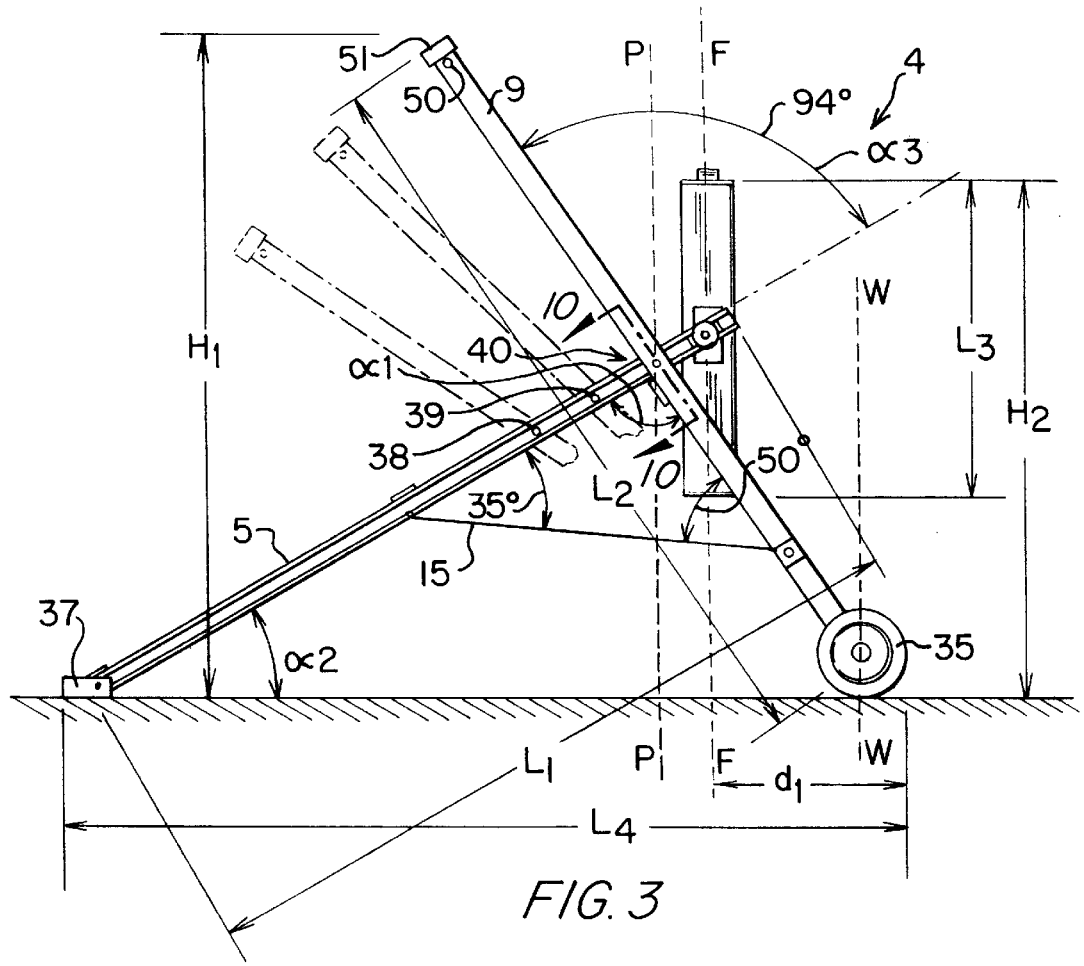
FIG. 3 is a side plan view of the preferred embodiment.

Referring next to FIG. 2 the sliding lock assembly 20 consists of an open channel leg 21 having an open channel 22 and lips 23,24. A plastic block 25 has grooves 26,27 to receive the lips 23,24. A hole 28 receives the bolt 29 which is permanently affixed to the brace 30. The brace 30 is fastened to the light panel 1 via holes 31 and bolts (not shown). Washers 32 allow for pivoting without appreciable wear the handle 33 locks the assembly 201. Referring next to FIG. 10 one embodiment of the sliding lock is shown as assembly 100. The open channel leg 21 still houses a sliding block 250 which has a threaded hole to receive the bolt/handle 101. The washer 102 reduces wear.

Referring next to FIG. 3 safety tether 15 can be adjusted in length to allow $d_1$ to equal zero, wherein the light panel 1 is supported in plane W—W over the wheel 35. Angle usually ranges between 40–110 degrees. Holes 38,39,40 along leg 5 (and parallel holes in leg 6) allow the front legs 9,10 to adjust downward, wherein leg 9 is shown in dots to move backwards, thereby supporting the light panel 1 further forward toward plane W—W of wheel 35. /Rear legs 5,6 may have a ladder type pivoting brake 37. Nominal dimensions are $H_1=H_2$ 36 ½ inches, $d_1=11$ inches, $W_2=17$ ⅛ inches, $W_1=32$ ¼ inches, $_1$, $=_3=94$ degrees, $_2=30$ degrees; $L_1=L_2=56$ inches, $L_5=42$ inches, $L_4=65$ inches.

Figure 4:
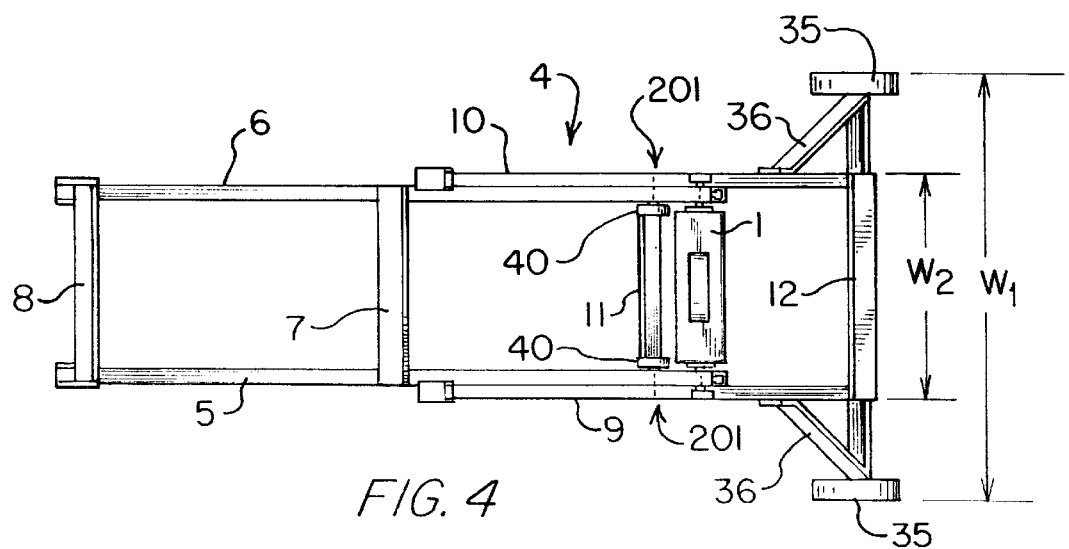
FIG. 4 is a top plan view of the stand.

Referring next to FIG. 4 the brackets 36 support the wheels 35, and they also widen the stance of the stand 4 which has a relatively narrow width $W_2=17$ ⅛ inches. The handles 40 of sliding lock assembly 201 can be seen.

Referring next to FIG. 5 legs 5 (and 6 not shown) can be slidingly adjusted along legs 9 (and 10 not shown) to form a high stance. The light panel 1 could be pivoted upward to light up the undercarriage of a car which is on a jack. This system provides very flexible total lighting for a garage shop area. Nominal dimensions are $H_{20}=65$ ¼ inches, $L_5=42$ inches, $_4=103$ degrees $_5=30$ degrees , $_{11}=47$ degrees. Dotted figures of leg 9 show the options using holes 38,39 to align with hole 50 of leg 9 for the sliding lock assembly 20 and the equivalent to bolt 29 shown in FIG. 2 a stopper 51 can be used on all legs for safety.

Referring next to FIG. 6 the light panel 1 has a rectangular frame 60, a shatter resistant lens 62 and safety crossbars 63,64,65 to prevent damage to the lens 62 and bulbs (not shown) when a tool is dropped onto the light panel 1.

Referring next to FIG. 7,8 an alternate embodiment safety lock 700 is shown to have a locking plate to having grooves 71. A tongue 73 is formed in open channel street 74 to engage the desired groove 71. A bolt 75, block 76 and nut 72 lock the safety lock 700, thereby replacing a safety tether.

Referring next to FIG. 9 a wide stance stand 90 has a wider pair of front legs 92, 93, wherein $W_9=25$ ⅝ inches. Caster type wheels 96 (either two or four) are used since no bracket 36 is needed. Light panel 99 has four bulbs ideal for medical use.

Although the present invention has been described with reference to preferred embodiments, numerous modifications and variations can be made and still the result will come within the scope of the invention. No limitation with respect to the specific embodiments disclosed herein is intended or should be inferred.

I claim:

1. A light panel stand comprising:
   a front pair of parallel support legs having a front support braces forming a front rigid assembly;
   a rear pair of parallel support legs having a rear support braces forming a rear rigid assembly;
   a hinge joining the front and rear rigid assemblies together in a folded and a range of open positions forming a central vertical plane intersecting the front and rear pair of parallel support legs, wherein the open positions form a double-inverted V-frame;
   a lock for the front and rear rigid assemblies to vary an angle between the front pair and rear pair of parallel support legs;
   said rear pair of parallel support legs having an extension forward over the front pair of parallel support legs and forward of the central vertical plane;
   said lock having sliding engagement with said front pair of parallel support legs; and
   a pair of light panel supports pivotably supporting a light panel between the front and rear rigid assemblies and above the front support braces.

2. The stand of claim 1, wherein the front pair and the rear pair pair of parallel support legs each have a caster on each member of the pair, thereby providing a mobile stand.

3. The stand of claim 1, wherein the light panel support bolts further comprise a pair of handles having nuts to lock the pair of bolts.

4. The stand of claim 1, wherein the hinge further comprises a bolt and a nut.

5. The stand of claim 1, wherein the front pair of parallel legs further comprises a plurality of forward pitch adjustment holes for supporting said rear pair of parallel support legs at a selectable forward pitch.

6. The stand of claim 1, wherein the sliding engagement further comprises an open channel support leg having a sliding block inside the open channel.

7. The stand of claim 6, wherein the lock further comprises a bolt through the open channel support leg and into sliding block to enable a tightening of the sliding block against a lip of the open channel support leg.

8. The stand of claim 1, wherein the lock further comprises a bolt through the open channel support leg and a hole in a member of the front pair of parallel support legs.

9. The stand of claim 1, wherein the pair of light panel supports further comprises an adjustable lock along top ends of said rear pair of parallel support legs.

10. The stand of claim 9, wherein the adjustable lock further comprises an open channel support leg having a sliding block therein and a locking bolt to tighten the sliding block against a lip of said open channel.

11. The stand of claim 9, wherein the rear pair of parallel support legs each has an end stop to prevent the light panel from inadvertent disconnection therefrom.

12. The stand of claim 1, further comprising a tether brace between a left member of said rear pair of parallel support legs and a left member of said front pair of parallel support legs.

13. The stand of claim 12, wherein said tether brace has a connection to said left rear member which is above a connection to said left front member, therein enabling a range of angles between said front pair and rear pair ranging between 0 and 180 degrees.

14. The stand of claim 1, wherein a distance between a right and left member of said front pair of parallel support legs ranges from six inches to twenty four inches, and each left and right member has a wheel bracket and wheel extending sideways to increase a base support width and provide mobility.

15. The stand of claim 1, wherein the light panel further comprises a lens door supporting a shatter resistant lens and the lens door has a support braces supporting the lens.

16. A light panel stand comprising:
   a front pair of parallel support legs having a front support braces forming a front rigid assembly;
   a rear pair of parallel support legs having a rear support braces forming a rear rigid assembly;
   a hinge means joining the front and rear rigid assemblies together in a folded and a range of open positions forming a central vertical plane intersecting the front and rear pair of parallel support legs, wherein the open positions form a double-inverted V-frame;
   a lock means for the front and rear rigid assemblies to vary an angle between the front pair and rear pair of parallel support legs;
   said rear pair of parallel support legs having an extension forward over the front pair of parallel support legs and forward of the central vertical plane;
   said a lock means having sliding engagement with said rear pair of parallel support legs; and
   a pair of light panel supports pivotably supporting a light panel between the front and rear rigid assemblies and above the front support braces.

17. The stand of claim 16, wherein the front pair and the rear pair pair of parallel support legs each have a caster on each member of the pair, thereby providing a mobile stand.

18. The stand of claim 16, wherein the light panel support bolts further comprise a pair of handles having nuts to lock the pair of bolts.

19. The stand of claim 16, wherein the hinge further comprises a bolt and a nut.

20. The stand of claim 16, wherein the rear pair of parallel legs further comprises a plurality of forward pitch adjustment holes for supporting said front pair of parallel support legs at a selectable forward pitch.

* * * * *